(12) United States Patent
Chung et al.

(10) Patent No.: US 12,392,911 B2
(45) Date of Patent: Aug. 19, 2025

(54) METHOD OF MEASURING ABSORBED DOSE OF RADIATION IN SMALL IRRADIATION FIELDS

(71) Applicants: SEOUL NATIONAL UNIVERSITY R&DB FOUNDATION, Seoul (KR); IUCF-HYU (INDUSTRY-UNIVERSITY COOPERATION FOUNDATION HANYANG UNIVERSITY), Seoul (KR)

(72) Inventors: Hyun Tai Chung, Seoul (KR); Tae Hoon Kim, Seoul (KR); Yong Kyun Kim, Sejong (KR)

(73) Assignees: Seoul National University R&DB Foundation, Seoul (KR); IUCF-HYU (Industry-University Cooperation Foundation Hanyang University), Seoul (KR)

( * ) Notice: Subject to any disclaimer, the term of this patent is extended or adjusted under 35 U.S.C. 154(b) by 212 days.

(21) Appl. No.: 18/366,317

(22) Filed: Aug. 7, 2023

(65) Prior Publication Data

US 2023/0375721 A1    Nov. 23, 2023

Related U.S. Application Data

(63) Continuation of application No. PCT/KR2021/019555, filed on Dec. 22, 2021.

(30) Foreign Application Priority Data

Mar. 23, 2021    (KR) .................. 10-2021-0037457

(51) Int. Cl.
*G01T 1/20*  (2006.01)
*G01T 1/02*  (2006.01)
*G01T 7/00*  (2006.01)

(52) U.S. Cl.
CPC ............. *G01T 1/023* (2013.01); *G01T 7/005* (2013.01)

(58) Field of Classification Search
None
See application file for complete search history.

(56) References Cited

U.S. PATENT DOCUMENTS

| 8,447,012 B2 | 5/2013 | Ichizawa et al. |
| 9,462,990 B2 * | 10/2016 | Kuwabara ................ A61B 6/54 |
| 2020/0233100 A1 * | 7/2020 | Rothschild ............ G01T 1/2018 |

FOREIGN PATENT DOCUMENTS

| JP | 5396684 B2 | 1/2014 |
| KR | 10-0267615 B1 | 10/2000 |

(Continued)

OTHER PUBLICATIONS

International Search Report issued for Korean Application No. PCT/KR2021/019555 dated Jun. 22, 2022 (2 Pages English, 2 Pages Korean).

*Primary Examiner* — Hoon K Song
(74) *Attorney, Agent, or Firm* — NSIP Law

(57) ABSTRACT

The present disclosure relates to a method of measuring an absorbed dose of radiation in small irradiation fields. The method of measuring an absorbed dose of radiation in small irradiation fields, includes an acquisition step of acquiring absorbed dose distribution data of radiation; a determination step of determining a region where an absorbed dose of radiation of a predetermined ratio or more is absorbed based on the absorbed dose distribution data of radiation; a formation step of forming a scintillator having a shape in which a plurality of hexahedral cells are coupled to have a shape matching the region; a measurement step of measuring a absorbed dose of radiation irradiating the scintillator from a radiation irradiation device; and a calculation step of calcu- (Continued)

lating the absorbed dose of radiation of the cell at a predetermined position by using predetermined Equations.

6 Claims, 7 Drawing Sheets

(56) References Cited

FOREIGN PATENT DOCUMENTS

| KR | 10-1051126 B1 | 7/2011 |
| KR | 10-1641946 B1 | 7/2016 |
| KR | 10-1814930 B1 | 1/2018 |
| KR | 10-2018-0079681 A | 7/2018 |
| KR | 10-2021-0020558 A | 2/2021 |

\* cited by examiner

METHOD OF MEASURING ABSORBED DOSE OF RADIATION IN SMALL IRRADIATION FIELDS

CROSS-REFERENCE TO RELATED APPLICATION

This Application is a continuation application of PCT Application No. PCT/KR2021/019555 filed on Dec. 22, 2021, which claims the benefit of Korean Patent Application No. 10-2021-0037457 filed on Mar. 23, 2021, the entire disclosures of which are incorporated herein by reference.

BACKGROUND

1. Field

The present disclosure relates to a method of measuring an absorbed dose of radiation in small irradiation fields, and more particularly, to a method of measuring an absorbed dose of radiation in small irradiation fields capable of minimizing an error in a measurement result of an absorbed dose of radiation in small irradiation fields according to a volume average effect.

2. Description of the Related Art

Radiation therapy technology is a technology that is widely used in cancer treatment along with anticancer treatment and surgery, and is a technology that treats cancer by irradiating cancer cells with radiation by radiation equipment to suppress the growth of cancer cells and cause them to die.

In general, radiation therapy undergoes steps of establishing a treatment plan by calculating absorbed dose data of radiation by simulating an absorbed dose of radiation to be irradiated to cancer cells, etc., and verifying the result by measuring an actual absorbed dose of radiation.

In order to increase the effect of the radiation therapy technology and reduce side effects thereof, it is necessary to irradiate the patient with an appropriate absorbed dose of radiation. To this end, it is necessary to verify whether the actual absorbed dose of radiation irradiated from a radiation irradiation device matches the absorbed dose data of radiation.

Therefore, if the actually irradiated absorbed dose of radiation is not accurately measured, it is difficult to accurately control the quality of the radiation irradiation device based thereon. Accordingly, it is impossible to irradiate the patient with an appropriate absorbed dose of radiation.

On the other hand, a conventional method of measuring an absorbed dose of radiation in which the size of a radiation beam is similar to or smaller than the size of a detector (hereinafter, referred to as radiation in small irradiation fields) has a problem in that the absorbed dose of radiation in small irradiation fields actually irradiated is not accurately measured.

FIG. 1 is a graph showing results of measuring an absorbed dose of radiation by a conventional method.

For example, referring to FIG. 1, in the conventional method of measuring an absorbed dose of radiation, since the detector active volume is bigger than the measurement point, an error occurs in the measurement result of an absorbed dose of radiation of an active part for which the absorbed dose of radiation is to be known (hereinafter referred to as the volume average effect).

Therefore, it is necessary to calculate a volume average correction factor capable of correcting the error due to the volume average effect and to calculate the absorbed dose of radiation corrected for the error due to the volume average effect using the calculated volume average correction factor.

SUMMARY

An object of the present disclosure is to provide a method of measuring an absorbed dose of radiation in small irradiation fields in which a volume average correction factor capable of correcting an error due to a volume average effect is calculated, and an error due to the volume average effect is corrected using the calculated volume average correction factor.

Another object of the present disclosure is to provide a method of measuring an absorbed dose of radiation in small irradiation fields using a scintillator that may be manufactured at a reasonable cost.

The objects of the present disclosure are not limited to the tasks mentioned above, and other tasks not mentioned will be clearly understood by those skilled in the art from the description below.

As technical means for achieving the above technical problem, a method of measuring an absorbed dose of radiation in small irradiation fields according to an embodiment of the present disclosure includes an acquisition step of acquiring absorbed dose distribution data of radiation; a determination step of determining a region where an absorbed dose of radiation of a predetermined ratio or more is absorbed based on the absorbed dose distribution data of radiation; a formation step of forming a scintillator having a shape in which a plurality of hexahedral cells are coupled to have a shape matching the region; a measurement step of measuring a absorbed dose of radiation irradiating the scintillator from a radiation irradiation device; and a calculation step of calculating the absorbed dose of radiation of the cell at a predetermined position by using predetermined Equations.

In addition, the scintillator may be formed of plastic.

In addition, in the formation step, the scintillator may be formed by using 3D printing.

In addition, the predetermined ratio may be 90 percent or more and 100 percent or less.

In addition, a length of each side of the cell may have a positive length value of 1 mm or less.

In addition, in the measurement step, the scintillator may be coupled to a scintillator accommodating device including an adapter cap and a probe adapter to measure the absorbed dose of radiation.

Details of other embodiments for solving the problem are included in the description and drawings of the invention.

According to the means for solving the problems of the present disclosure described above, in the method of measuring an absorbed dose of radiation in small irradiation fields according to the present disclosure, the volume average correction factor may be calculated by measuring the absorbed dose of radiation in small irradiation fields using the scintillator having a shape matching the absorbed dose distribution region of radiation. Therefore, the error due to the volume average effect is corrected to provide the effect of accurately measuring the absorbed dose of radiation in the small irradiation fields.

In addition, since the absorbed dose of radiation in the small irradiation fields is more accurately measured, an appropriate absorbed dose of radiation may be irradiated to the patient based thereon, thereby providing an effect of effectively treating the patient.

In addition, the scintillator used in the method of measuring an absorbed dose of radiation in small irradiation fields is formed by using 3D printing, thereby providing an effect of measuring the absorbed dose of radiation in small irradiation fields at a reasonable cost.

DETAILED DESCRIPTION

Figure 1:
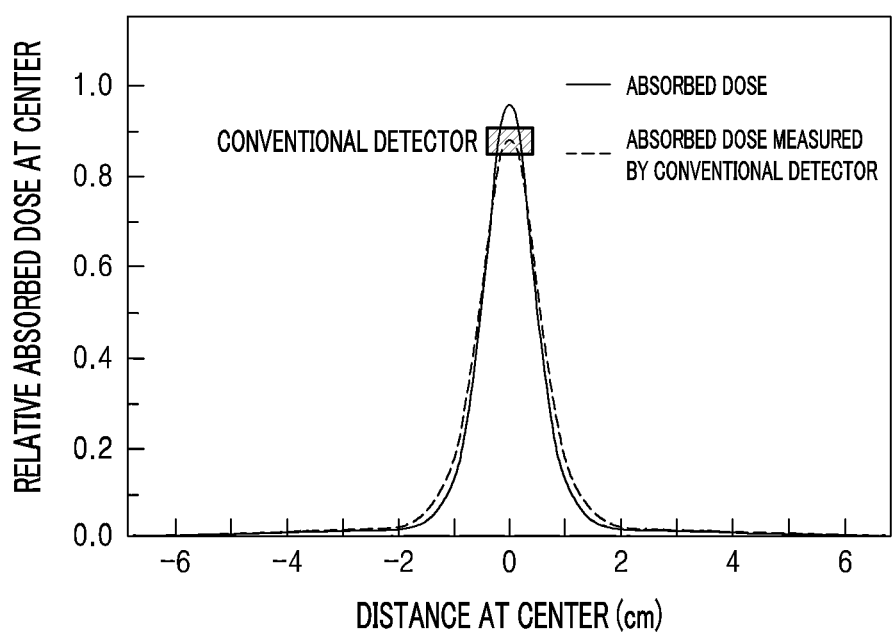
FIG. 1 is a graph illustrating results of measuring an absorbed dose of radiation in small irradiation fields by a conventional method.

Hereinafter, embodiments of the present application will be described in detail so that those skilled in the art may easily practice with reference to the accompanying drawings. However, the present disclosure may be implemented in many different forms and is not limited to the embodiments described herein. In addition, in order to clearly describe the present application in the drawings, parts irrelevant to the description are omitted, and similar reference numerals are attached to similar parts throughout the specification.

Throughout the present specification, when a part is said to be "connected" to another part, this includes not only a case of being "directly connected" but also a case of being "electrically connected" with another element therebetween.

Throughout the present specification, when a member is said to be located "on" another member, this includes not only a case where the member is in contact with another member, but also a case where another member exists between the two members.

Throughout the present specification, when a part "includes" a certain component, it means that it may further include other components without excluding other components unless otherwise stated. As used throughout the present specification, the terms "about," "substantially," and the like are used at or approximating the value when manufacturing and material tolerances inherent in the stated meaning are given, and do not convey the understanding of this application. Accurate or absolute figures are used to help prevent exploitation by unscrupulous infringers of the disclosed disclosure. The term "step of (doing)" or "step of" as used throughout the present specification does not mean "step for".

Hereinafter, preferred embodiments of the present disclosure will be described in detail with reference to the accompanying drawings and the description below. However, the present disclosure is not limited to the embodiments described herein and may be embodied in other forms. Like reference numbers indicate like elements throughout the specification.

Hereinafter, a method of measuring an absorbed dose of radiation in small irradiation fields according to an embodiment of the present disclosure will be described.

Figure 2:
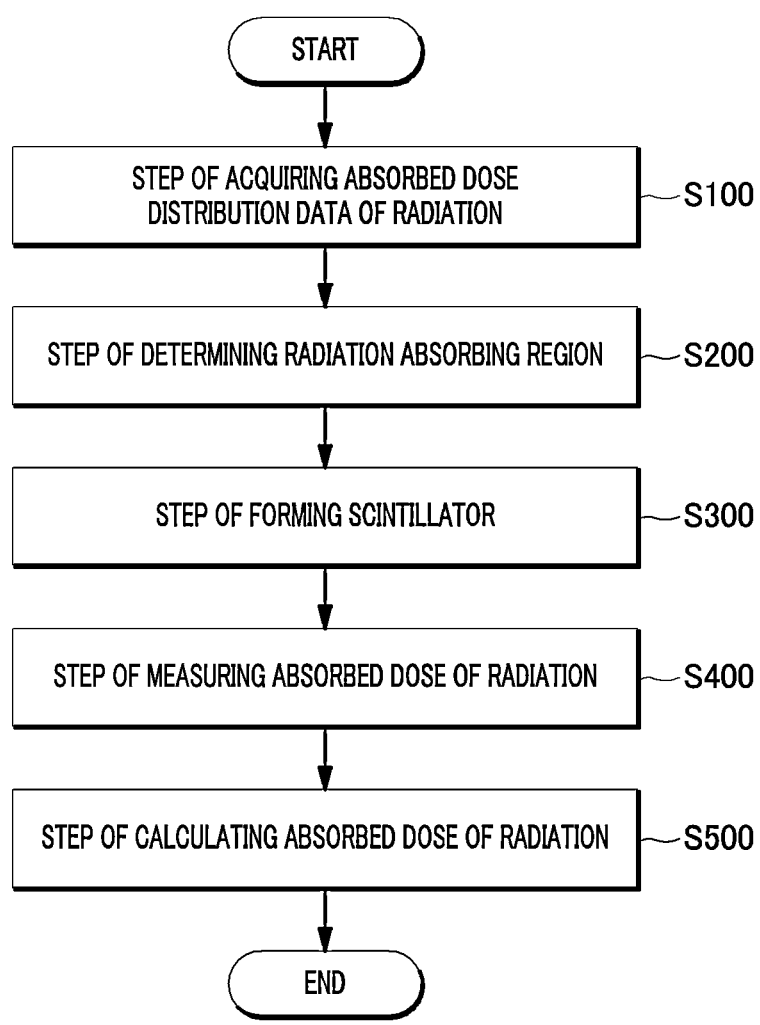
FIG. 2 is a flowchart illustrating a method of measuring an absorbed dose of radiation in small irradiation fields according to an embodiment of the present disclosure.

FIG. 2 is a flowchart illustrating a method of measuring an absorbed dose of radiation in small irradiation fields according to an embodiment of the present disclosure.

Referring to FIG. 2, the method of measuring an absorbed dose of radiation in small irradiation fields according to an embodiment of the present disclosure includes an acquisition step S100, a determination step S200, a formation step S300, a measurement step S400, and a calculation step S500.

First, the acquisition step S100 will be described.

The acquiring step S100 is a step of acquiring absorbed dose distribution data of radiation irradiated from the radiation device.

The absorbed dose distribution data of radiation is data calculated by simulating the absorbed dose of radiation to be irradiated from the radiation irradiation device, and is generally disclosed to a user. Therefore, the user may obtain the absorbed dose distribution data of radiation of the radiation irradiation device for which absorbed dose of radiation is to be measured from open data.

Next, the determination step S200 will be described.

The determination step S200 is a step of determining a region where an absorbed dose of radiation of a predetermined ratio or more is absorbed based on the absorbed dose distribution data of radiation.

Figure 3A:
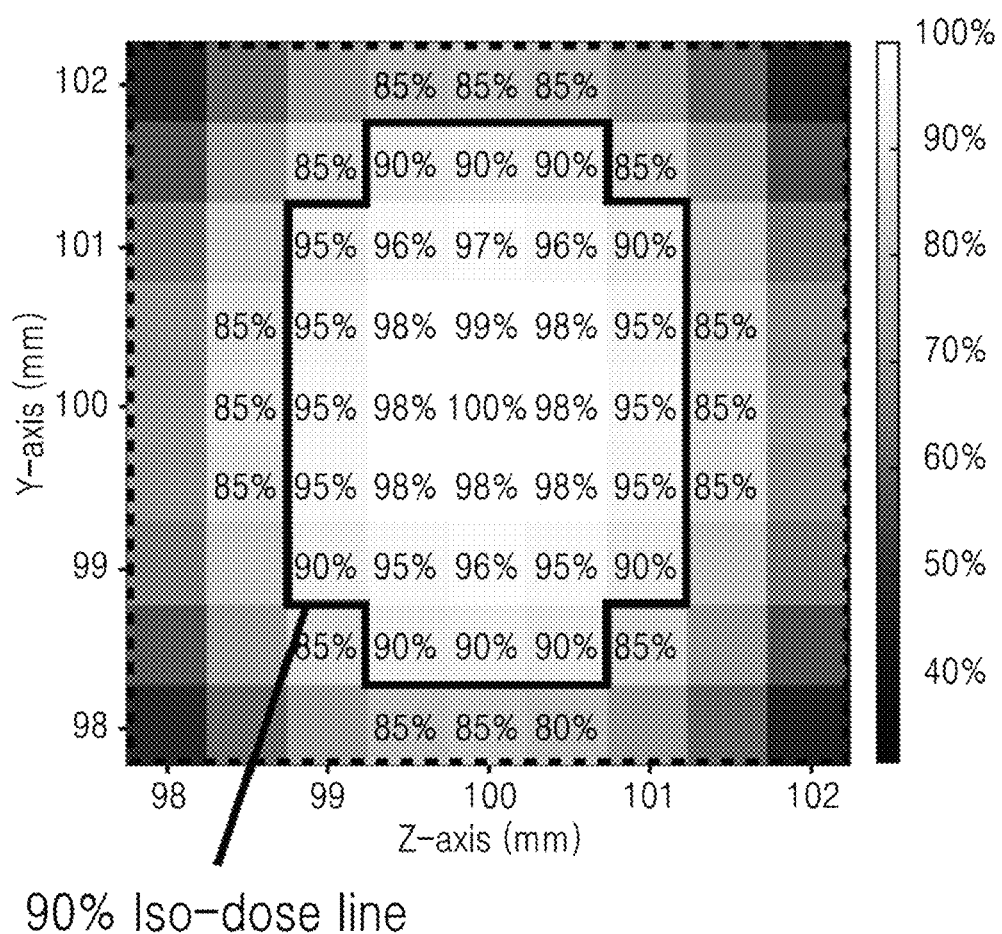
FIG. 3A is a diagram illustrating a predetermined absorbed dose distribution plane of radiation in which a region where 90 percent or more of the absorbed dose of radiation is absorbed is determined.

FIG. 3A is a diagram illustrating a predetermined absorbed dose distribution plane of radiation in which a region where 90 percent or more of the absorbed dose of radiation is absorbed is determined.

For example, referring to FIG. 3A, it is possible to determine a region where 90 percent or more of the absorbed dose of radiation is absorbed among the absorbed dose distribution regions of radiation on a YZ plane based on the acquired absorbed dose distribution data of radiation.

In addition, although not illustrated in the drawing, a predetermined region may be determined such that 90 percent or more of the absorbed dose of radiation on an XY plane and a ZX plane as well as the YZ plane is absorbed.

Figure 3B:
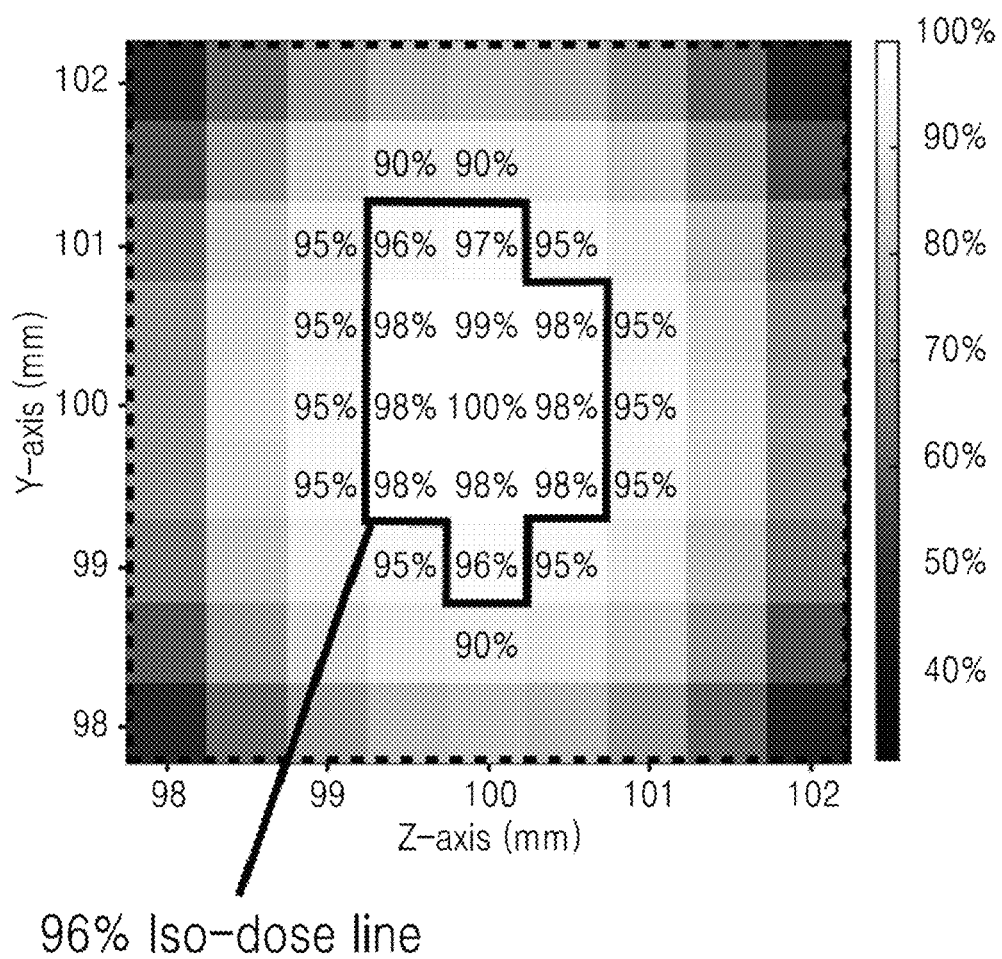
FIG. 3B is a diagram illustrating a predetermined absorbed dose distribution plane of radiation in which a region where 96 percent or more of the absorbed dose of radiation is absorbed is determined.

FIG. 3B is a diagram illustrating a predetermined absorbed dose distribution plane of radiation in which a region where 96 percent or more of the absorbed dose of radiation is absorbed is determined.

As another example, referring to FIG. 3B, it is possible to determine a region where 96 percent or more of the absorbed dose of radiation is absorbed among the absorbed dose distribution regions of radiation on the YZ plane based on the acquired absorbed dose distribution data of radiation.

In addition, although not illustrated in the drawing, a predetermined region may be determined such that 96 percent or more of the absorbed dose of radiation on the XY plane and the ZX plane as well as the YZ plane is absorbed.

In this way, in the determination step S200, it is possible to determine a region where the absorbed dose of radiation is a predetermined ratio or more selected by the user. For example, the user may select the predetermined ratio within a range of 90% or more and 100% or less.

Next, the formation step S300 will be described.

The formation step S300 is a step of forming the scintillator 10 to have a shape that matches a region where the absorbed dose of radiation determined in the determination step S200 is absorbed.

In general, since the absorbed dose distribution data of radiation provides information on the absorbed dose distribution of radiation in a form of a set of a plurality of hexahedral voxels, the region where the absorbed dose of radiation determined in the determination step S200 is absorbed is the form of the set of the plurality of hexahedral voxels Therefore, the scintillator 10 having the shape matching the region where the absorbed dose of radiation formed in the formation step S300 is absorbed may be formed in a shape in which a plurality of hexahedral cells are coupled.

Figure 4A:
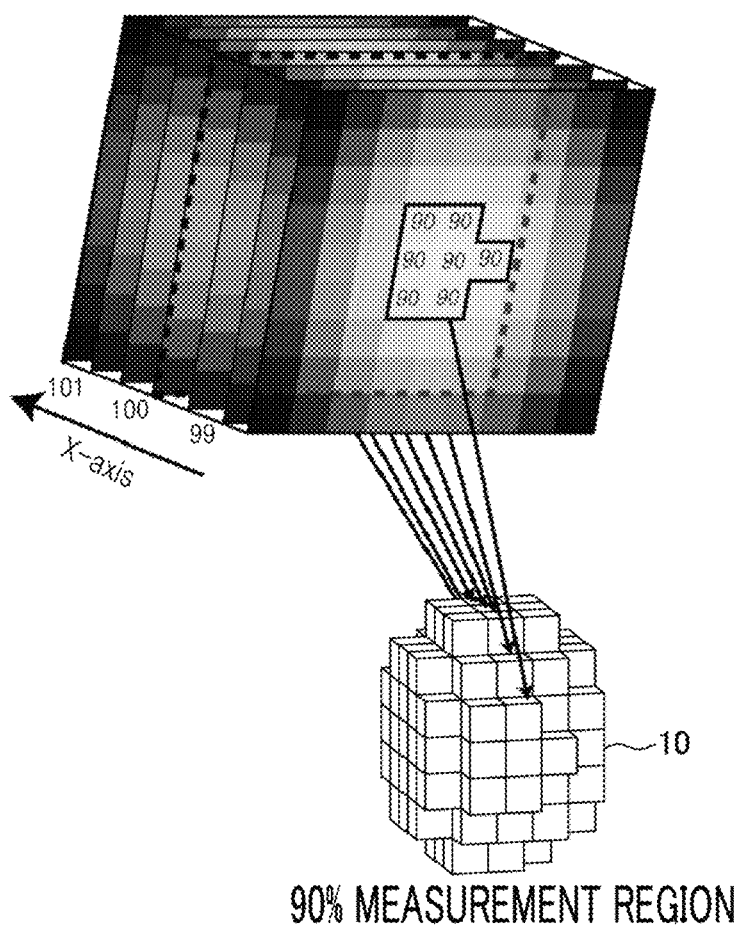
FIG. 4A is a view illustrating a scintillator formed to have a shape corresponding to the region determined in FIG. 3A.

FIG. 4A is a view illustrating a scintillator formed to have a shape corresponding to the region determined in FIG. 3A.

For example, referring to FIG. 4A, the scintillator 10 may be formed in a shape in which a plurality of hexahedral cells are coupled in a shape matching the region determined in FIG. 3A.

Figure 4B:
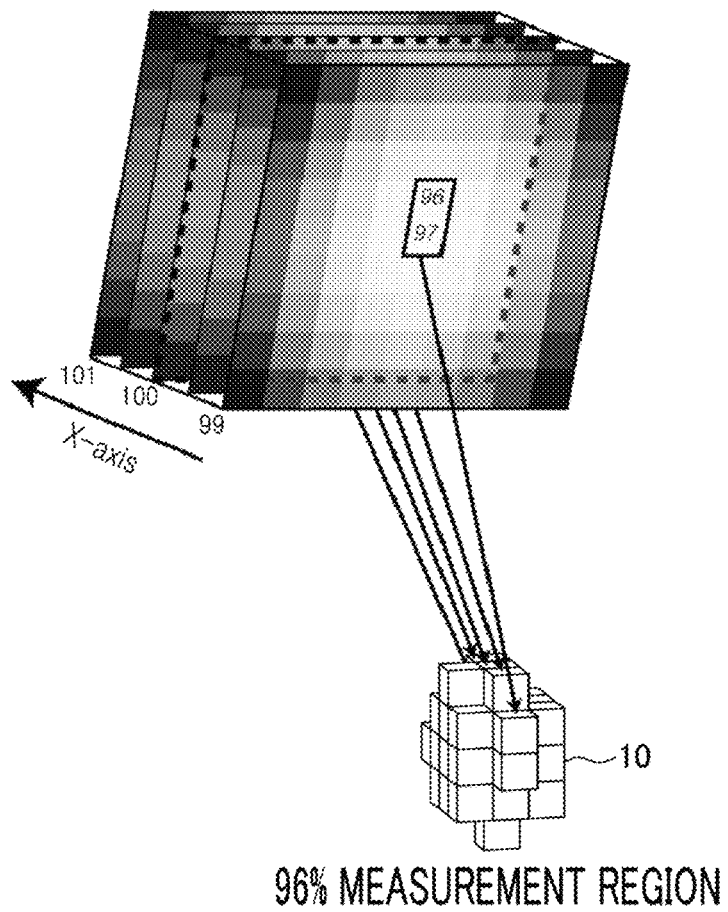
FIG. 4B is a view illustrating a scintillator formed to have a shape corresponding to the region determined in FIG. 3B.

FIG. 4B is a view illustrating a scintillator formed to have a shape corresponding to the region determined in FIG. 3B.

As another example, referring to FIG. 4B, the scintillator 10 may be formed in a shape in which a plurality of hexahedral cells are coupled in a shape matching the region determined in FIG. 3B.

On the other hand, the scintillator 10 may be formed of plastic using 3D printing technology. For example, the scintillator 10 may be formed of plastic by 3D printing to have a shape in which hexahedral cells are coupled with a length of each side having a positive length value of 1 mm or less.

Next, the measurement step S400 will be described.

The measurement step S400 is a step of measuring the absorbed dose of radiation irradiating the scintillator 10 formed in the formation step S300 from the radiation irradiation device.

Figure 5:
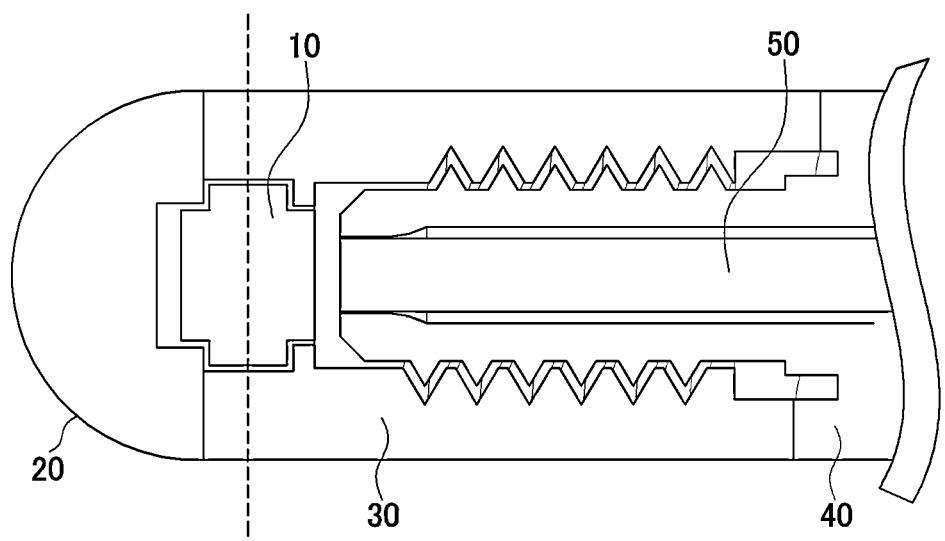
FIG. 5 is a view illustrating a scintillator coupled to a scintillator accommodating device.

FIG. 5 is a view illustrating the scintillator coupled to a scintillator accommodating device.

For example, as illustrated in FIG. 5, the scintillator accommodating device may include a probe 40 including an optical fiber core 50, and an adapter 30 coupled to the probe 40 and manufactured in a shape corresponding to the shape of the scintillator 10, an adapter cap 20 coupled to the adapter 30 and manufactured in a shape corresponding to the shape of the scintillator 10.

By installing the scintillator 10 to the adapter 30 of the scintillator accommodating device and irradiating radiation from the radiation irradiation device to the scintillator accommodating device, the absorbed dose of radiation irradiated from the irradiation device may be measured.

Next, the calculation step S500 will be described.

The calculation step S500 is a step of calculating the absorbed dose of radiation of a cell located at a predetermined position of the scintillator 10.

A total absorbed dose of radiation absorbed by the scintillator 10 may be calculated by 'Equation 1' below.

$$D_d = \sum_{i,j,k} D(i, j, k) = D(a, b, c) \sum_{i,j,k} \frac{D(i, j, k)}{D(a, b, c)} \qquad \text{[Equation 1]}$$

(Dd is the total absorbed dose of radiation measured by the scintillator, $D(i,j,k)$ is an absorbed dose of radiation of the cell located at the i-th in the x-axis direction, the j-th in the y-axis direction, and the k-th in the z-axis direction on the three-dimensional coordinate system based on the cell located at a predetermined position of the scintillator, and $D(a,b,c)$ is an absorbed dose of radiation of the cell located at the a-th in the x-axis direction, the b-th in the y-axis direction, and the c-th in the z-axis direction on the three-dimensional coordinate system based on the cell located at a predetermined position of the scintillator)

On the other hand, 'Equation 3' below may be derived by substituting 'Equation 2' into 'Equation 1'.

$$\delta_{i,j,k} = \frac{D(i, j, k)}{D(a, b, c)} \qquad \text{[Equation 2]}$$

($D(a,b,c)$ is an absorbed dose of radiation of the cell located at the a-th in the x-axis direction, the b-th in the y-axis direction, and the c-th in the z-axis direction on the three-dimensional coordinate system based on the cell located at a predetermined position of the scintillator, and $D(i,j,k)$ is an absorbed dose of radiation of the cell located at the i-th in the x-axis direction, the j-th in the y-axis direction, and the k-th in the z-axis direction on the three-dimensional coordinate system based on the cell located at a predetermined position of the scintillator)

$$D_d = \sum_{i,j,k} D(i, j, k) = D(a, b, c) * \sum_{i,j,k} \delta(i, j, k) \qquad \text{[Equation 3]}$$

(Dd is the total absorbed dose of radiation measured by the scintillator, $D(i,j,k)$ is an absorbed dose of radiation of the cell located at the i-th in the x-axis direction, the j-th in the y-axis direction, and the k-th in the z-axis direction on the three-dimensional coordinate system based on the cell located at a predetermined position of the scintillator, $D(a,b,c)$ is an absorbed dose of radiation of the cell located at the a-th in the x-axis direction, the b-th in the y-axis direction, and the c-th in the z-axis direction on the three-dimensional coordinate system based on the cell located at a predetermined position of the scintillator, and $$\sum_{i,j,k} \delta(i, j, k)$$

is information included in the absorbed dose distribution data of radiation)

In addition, 'Equation 4' below may be derived from 'Equation 3'.

$$D(a, b, c) = \left( \frac{1}{\sum_{i,j,k} \delta_{i,j,k}} \right) * D_d \qquad \text{[Equation 4]}$$

($D(a,b,c)$ is the absorbed dose of radiation of the cell located at the a-th in the x-axis direction, the b-th in the y-axis direction, and the c-th in the z-axis direction on the three-dimensional coordinate system based on the cell located at a predetermined position of the scintillator. Dd is the total absorbed dose of radiation measured by the scintillator, and $$\sum_{i,j,k} \delta(i, j, k)$$

is the information included in the absorbed dose distribution data of radiation)

Next, 'Equation 5' below may be derived by modifying 'Equation 4'.

$$D(a, b, c) = \left(\frac{1}{\sum_{i,j,k} \delta_{i,j,k}}\right) * D_d = \frac{Vcell}{\sum_{i,j,k} \delta_{i,j,k}} * \frac{Dd}{Vcell} \quad \text{[Equation 5]}$$

(D(a,b,c) is the absorbed dose of radiation of the cell located at the a-th in the x-axis direction, the b-th in the y-axis direction, and the c-th in the z-axis direction on the three-dimensional coordinate system based on the cell located at a predetermined position of the scintillator, Dd is the total absorbed dose of radiation measured by the scintillator, Vcell is the volume of the scintillator, and $$\sum_{i,j,k} \delta(i, j, k)$$

is the information included in the absorbed dose distribution data of radiation)

Next, 'Equation 8' may be derived by substituting the following 'Equation 6' and 'Equation 7' into 'Equation 5'.

$$k_v = \left[\frac{Vcell}{\sum_{i,j,k} \delta_{i,j,k}}\right] \quad \text{[Equation 6]}$$

(Kv is the volume average correction factor, Vcell is the volume of the scintillator, and $$\sum_{i,j,k} \delta(i, j, k)$$

is the information included in the absorbed dose distribution data of radiation)

$$Dm = \frac{Dd}{Vcell} \quad \text{[Equation 7]}$$

(Dm is the average absorbed dose of radiation measured by the scintillator, Dd is the total absorbed dose of radiation measured by the scintillator, and Vcell is the volume of the scintillator)

$$D(a,b,c) = Kv * Dm \quad \text{[Equation 8]}$$

(D(a,b,c) is the absorbed dose of radiation of the cell located at the a-th in the x-axis direction, the b-th in the y-axis direction, and the c-th in the z-axis direction on the three-dimensional coordinate system based on the cell located at a predetermined position of the scintillator, Kv is the volume average correction factor, and Dm is the average absorbed dose of radiation measured by the scintillator)

In conclusion, the absorbed dose of radiation of the cell located at the a-th in the x-axis direction, the b-th in the y-axis direction, and the c-th in the z-axis direction on the three-dimensional coordinate system based on the cell located at a predetermined position of the scintillator 10 may be calculated by obtaining the volume average correction factor Kv and the average absorbed dose of radiation Dm measured by the scintillator.

Among them, the volume average correction factor Kv may be calculated by recognizing the number of cells included in the scintillator 10 and using the information $$\sum_{i,j,k} \delta(i, j, k)$$

included in the obtained absorbed dose distribution data of radiation.

In addition, the average absorbed dose Dm of radiation measured by the scintillator 10, may be calculated by recognizing the total absorbed dose of radiation measured by the scintillator 10 and the volume of the scintillator 10. The volume of the scintillator 10 may be calculated by multiplying the volume of each cell by the total number of cells included in the scintillator 10, and may also be calculated by recognizing the length of each hexahedral cell.

On the other hand, unlike the scintillator 10 used in the method of measuring an absorbed dose of radiation in small irradiation fields according to an embodiment of the present disclosure, in the case of measuring the absorbed dose of radiation with the conventional scintillator, it is not possible to accurately calculate the absorbed dose of radiation at a predetermined position of the scintillator by using the above-described 'Equation 8'.

Figure 6:
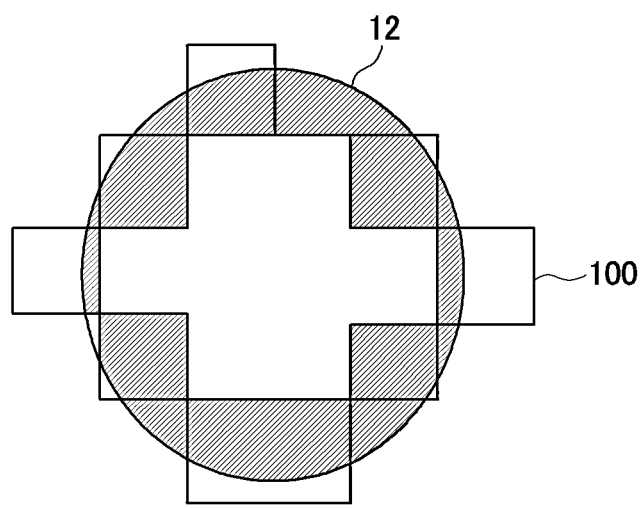
FIG. 6 is a diagram illustrating an absorbed dose distribution of radiation measured by a conventional scintillator.

FIG. 6 is a diagram illustrating an absorbed dose distribution of radiation measured by the conventional scintillator.

Specifically, referring to FIG. 6, when the absorbed dose distribution 100 of radiation is measured with a conventional scintillator 12 having a circular cross section, there are regions that include a part of the absorbed dose distribution 100 of radiation and do not include the absorbed dose distribution 100 of radiation at all among the regions of the scintillator 12.

Therefore, the total absorbed dose Dd of radiation measured using the scintillator 12 is different from the sum of all absorbed doses of radiation of the actual absorbed dose distribution 100 of radiation.

On the other hand, as described in 'Equation 8', in order to calculate the absorbed dose of radiation at a predetermined position of the scintillator 12, the information of the average absorbed dose of radiation, which is a value obtained by dividing the total absorbed dose Dd of radiation by the volume of the scintillator 12, is needed.

However, as described above, the total absorbed dose Dd of radiation measured by the scintillator 12 is different from the sum of all absorbed doses of radiation of the actual absorbed dose distribution 100 of radiation. Therefore, the calculated average absorbed dose of radiation also differs from the actual average absorbed dose of radiation.

Therefore, calculating the absorbed dose of radiation at a predetermined position of the scintillator 12 uses the calculated average absorbed dose of radiation different from the actual average absorbed dose of radiation. Therefore, the absorbed dose of radiation calculated at a predetermined position of the scintillator 12 is not accurate.

Hereinafter, the operation and effect of the method of measuring an absorbed dose of radiation in small irradiation fields according to an embodiment of the present disclosure will be described.

First, the user who wants to measure the absorbed dose of radiation of the radiation irradiation device obtains published absorbed dose distribution data of radiation. Then, the user determines a region where an absorbed dose of radiation of a predetermined ratio or more is absorbed based on the obtained absorbed dose distribution data of radiation.

Then, when the region where the absorbed dose of radiation is absorbed at a predetermined rate or more is determined, the user forms the scintillator 10 having a shape in which a plurality of hexahedral cells are coupled to have a shape matching the region where the absorbed dose of radiation is absorbed. At this time, the scintillator may be formed of plastic using 3D printing technology.

Next, the user measures the absorbed dose of radiation irradiated from the radiation irradiation device using the scintillator 10, and uses the above-described equations based on the measured absorbed dose of radiation and the obtained absorbed dose distribution data of radiation to calculate the absorbed dose of radiation of the cell at the predetermined position of the scintillator 10.

As described above, in the method of measuring an absorbed dose of radiation in small irradiation fields according to the present disclosure, the volume average correction factor may be calculated by measuring the absorbed dose of radiation in small irradiation fields using the scintillator having a shape matching the absorbed dose distribution region of radiation. Therefore, the error due to the volume average effect is corrected to provide the effect of accurately measuring the absorbed dose of radiation in the small irradiation fields.

In addition, since the absorbed dose of radiation in the small irradiation fields is more accurately measured, an appropriate absorbed dose of radiation may be irradiated to the patient based thereon, thereby providing an effect of effectively treating the patient.

In addition, the scintillator used in the method of measuring an absorbed dose of radiation in small irradiation fields is formed by using 3D printing, thereby providing an effect of measuring the absorbed dose of radiation in small irradiation fields at a reasonable cost.

The method according to an embodiment of the present disclosure may be implemented in a form of a recording medium including instructions executable by a computer, such as program modules executed by a computer. Computer readable media may be any available media capable of being accessed by a computer and includes both volatile and nonvolatile media, removable and non-removable media. In addition, computer readable media may include computer storage media. Computer storage media includes both volatile and nonvolatile, removable and non-removable media implemented in any method or technology for storage of information such as computer readable instructions, data structures, program modules or other data.

The above description of the present disclosure is for illustrative purposes, and those skilled in the art may understand that it may be easily modified into other specific forms without changing the technical spirit or essential features of the present disclosure. Therefore, the embodiments described above should be understood as illustrative in all respects and not limiting. For example, each component described as a single type may be implemented in a distributed manner, and similarly, components described as distributed may be implemented in a coupled form.

The scope of the present disclosure is indicated by the following claims rather than the above detailed description, and all changes or modifications derived from the meaning and scope of the claims and equivalent concepts thereof should be construed as being included in the scope of the present disclosure.

Form for Implementing the Invention

The mode for implementing the invention is the same as the best mode for implementing the invention described above.

INDUSTRIAL APPLICABILITY

The present disclosure relates to a method of measuring an absorbed dose of radiation in small irradiation fields, and since it may be used in the industry related to radiation therapy, it has industrial applicability.

What is claimed is:

1. A method of measuring an absorbed dose of radiation in small irradiation fields, comprising:
acquiring absorbed dose distribution data of radiation;
determining a region where an absorbed dose of radiation of a predetermined ratio or more is absorbed based on the absorbed dose distribution data of radiation;
forming a scintillator having a shape in which a plurality of hexahedral cells are coupled to have a shape matching the region;
measuring an absorbed dose of radiation irradiating the scintillator from a radiation irradiation device; and
calculating the absorbed dose of radiation of the cell at a predetermined position by using Equations 1 to 4, $$\delta_{i,j,k} = \frac{D(i, j, k)}{D(a, b, c)} \quad \text{[Equation 1]}$$

(D(a,b,c) is an absorbed dose of radiation of the cell located at the a-th in the x-axis direction, the b-th in the y-axis direction, and the c-th in the z-axis direction on the three-dimensional coordinate system based on the cell located at a predetermined position of the scintillator, and D(i,j,k) is an absorbed dose of radiation of the cell located at the i-th in the x-axis direction, the j-th in the y-axis direction, and the k-th in the z-axis direction on the three-dimensional coordinate system based on the cell located at a predetermined position of the scintillator)

$$k_v = \left[ \frac{Vcell}{\sum_{i,j,k} \delta_{i,j,k}} \right] \quad \text{[Equation 2]}$$

(Kv is the volume average correction factor, Vcell is the volume of the scintillator, and $$\sum_{i,j,k} \delta(i, j, k)$$

is the information included in the absorbed dose distribution data of radiation)

$$Dm = \frac{Dd}{Vcell} \qquad \text{[Equation 3]}$$

(Dm is the average absorbed dose of radiation measured by the scintillator, Dd is the total absorbed dose of radiation measured by the scintillator, and Vcell is the volume of the scintillator)

$$D(a,b,c) = Kr*Dm \qquad \text{[Equation 4]}$$

(D(a,b,c) is the absorbed dose of radiation of the cell located at the a-th in the x-axis direction, the b-th in the y-axis direction, and the c-th in the z-axis direction on the three-dimensional coordinate system based on the cell located at a predetermined position of the scintillator, Kv is the volume average correction factor, and Dm is the average absorbed dose of radiation measured by the scintillator).

2. The method of measuring an absorbed dose of radiation in small irradiation fields of claim 1, wherein the scintillator is formed of plastic.

3. The method of measuring an absorbed dose of radiation in small irradiation fields of claim 2, wherein in the formation step, the scintillator is formed by using 3D printing.

4. The method of measuring an absorbed dose of radiation in small irradiation fields of claim 3, wherein the predetermined ratio is 90 percent or more and 100 percent or less.

5. The method of measuring an absorbed dose of radiation in small irradiation fields of claim 3, wherein a length of each side of the cell has a positive length value of 1 mm or less.

6. The method of measuring an absorbed dose of radiation in small irradiation fields of claim 5, wherein in the measurement step, the scintillator is coupled to a scintillator accommodating device including an adapter cap and a probe adapter to measure the absorbed dose of radiation.

\* \* \* \* \*